(12) United States Patent
Lee et al.

(10) Patent No.: US 9,795,653 B2
(45) Date of Patent: Oct. 24, 2017

(54) USE OF INHALABLE POWDER FORMULATION COMPRISING GROWTH HORMONE FOR PREVENTING OR TREATING NMDA RECEPTOR HYPOFUNCTION-RELATED DISEASES

(71) Applicant: MediGeneBio Corporation, Yong-in Si (KR)

(72) Inventors: Sy Lee, Yongin-si (KR); Sung-Ick Park, Yongin-si (KR)

(73) Assignee: MediGeneBio Corporation, Yongin-si (KR)

( * ) Notice: Subject to any disclaimer, the term of this patent is extended or adjusted under 35 U.S.C. 154(b) by 0 days.

(21) Appl. No.: 14/180,677

(22) Filed: Feb. 14, 2014

(65) Prior Publication Data
US 2014/0162953 A1 Jun. 12, 2014

Related U.S. Application Data

(62) Division of application No. 13/511,451, filed as application No. PCT/KR2009/006970 on Nov. 25, 2009, now abandoned.

(51) Int. Cl.
*A61K 38/27* (2006.01)
*A61K 9/00* (2006.01)

(52) U.S. Cl.
CPC ............ *A61K 38/27* (2013.01); *A61K 9/0073* (2013.01); *A61K 9/0075* (2013.01)

(58) Field of Classification Search
None
See application file for complete search history.

(56) References Cited

U.S. PATENT DOCUMENTS 4,898,856 A * 2/1990 Aroonsakul .................. 514/171
7,008,644 B2 3/2006 Batycky et al.

FOREIGN PATENT DOCUMENTS

WO WO2005/004895 * 1/2005 ............. A61K 38/00

OTHER PUBLICATIONS

Metman et al., Neurology, 2002; 59: 694-699.*
Maler et al., Brain Research, 2005; 1052: 156-162.*
Bosquillon et al., Journal of Controlled Release, 2004; 96: 233-244.*
Li and Tsien, N Engl J Med. 2009; 361: 302-303.*
Lakhan et al., doi: 10.3389/fpsyt.2013.00052; 7 pages total.*
Lane et al., Arch Gen Psychiatry, 2005; 62: 1196-1204.*
Korean Intellectual Property Office, Office Action dated Feb. 27, 2014 issued in the corresponding Korean Application No. 2012-7016508.
Ramsey, et al., "Growth Hormone Treatment Attenuates Age-Related Changes in Hippocampal Short-Term Plasticity and Spatial Learning", Neuroscience 129 (2004), p. 119-127.

* cited by examiner

*Primary Examiner* — Christina Borgeest
(74) *Attorney, Agent, or Firm* — Sughrue Mion, PLLC

(57) ABSTRACT

A use of an inhalable powder formulation for preventing or treating an NMDA receptor hypofunction-related disease, a method for preventing or treating an NMDA receptor hypofunction-related disease in a subject, which comprises administering a therapeutically effective amount of an inhalable powder formulation comprising growth hormone (GH) to the subject in need thereof, and an inhalable powder formulation for preventing or treating an NMDA receptor hypofunction-related disease comprising GH as an active ingredient are provided.

5 Claims, 8 Drawing Sheets

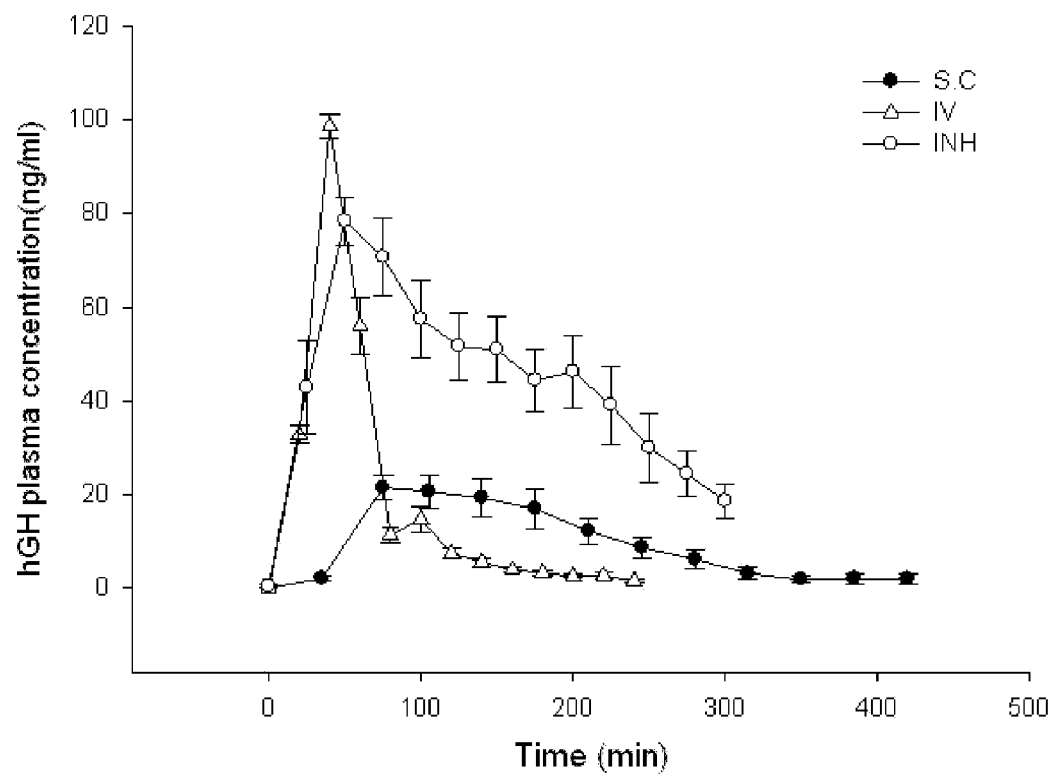

USE OF INHALABLE POWDER FORMULATION COMPRISING GROWTH HORMONE FOR PREVENTING OR TREATING NMDA RECEPTOR HYPOFUNCTION-RELATED DISEASES

CROSS-REFERENCE TO RELATED APPLICATIONS

This is a divisional application of U.S. patent application Ser. No. 13/511,451 (pending) filed May 23, 2012, which is a National Stage Application of PCT/KR2009/006970 filed Nov. 25, 2009, the contents of all of which are incorporated herein by reference in their entirety.

FIELD OF THE INVENTION

The present invention relates to a use of inhalable powder formulation comprising growth hormone for preventing or treating NMDA receptors hypofunction-related diseases.

BACKGROUND OF THE INVENTION

The indication of growth hormone (GH) replacement has gradually been expanding beyond the original indication for the growth hormone deficiency. The current list of GH replacement includes several genetic disorders characterized by the short stature such as Turner syndrome, Prader-Willi syndrome, and Noonan syndrome. In the Prader-Willi syndrome, GH is expected to be effective in the improvement of the body composition as well as the linear body growth (see, Mogul, H. R. et al., *J Clin Endocrinol Metab* 93 (4), 1238-1245 (2008)). Based on the efficacy results from the randomized studies, GH was approved by the U.S. Food and Drug Administration for treatment of the idiopathic short stature in children, whose predicted adult height is less than 2.25 SDS (see, Leschek, E. W. et al., *J Clin Endocrinol Metab* 89 (7), 3140-3148 (2004); and Wit, J. M. et al., *J Pediatr* 146 (1), 45-53 (2005)). The other indication of GH includes wasting from AIDS (Storer T W, W. L., et al., *J Clin Endocrinol Metab.* 90 (8), 4474-4482. (2005)). Given the broad range of biological benefits of GH, the expansion of GH indications is expected to continue.

On the other hand, one of the challenges in GH application is the compliance issue. While daily subcutaneous injections are needed for maintaining the clinical efficacy of GH, this has not been favored by the patients, especially the pediatric patients, leading to early termination of the therapy (Coste, J. et al., *BMJ* 315 (7110), 708-713 (1997)). In this respect, an inhalable formulation of GH can be considered as a potential alternative. The lung is an unique portal for systemic drug delivery because of the large surface area for drug absorption (~100 m$^2$ in adults) (Patton, J. S., *Advanced Drug Delivery Reviews* 19 (1), 3 (1996)), good epithelial permeability, and a rich blood supply (Schanker, L. L. S., *Biochemical pharmacology* 27 (4), 381-385 (1978); and Patton, J. S., *Proc Am Thorac Soc* 1 (4), 338-344 (2004)).

Furthermore, drugs deposited in the lungs face relatively lower concentrations of drug-metabolizing enzymes than those delivered orally (Patton, J. S., Advanced Drug Delivery Reviews 19 (1), 3 (1996); and Ann, T. et al., *Journal of pharmaceutical sciences*, 92 (6), 1216-1233 (2003)). This property is particularly beneficial for delivery of protein drugs like GH, whose administration is currently limited to parenteral routes. Accordingly, the lung has gained increasing attention as a potential site for systemic delivery of drugs with poor oral bioavailability, as evident from recent advancement of inhalable insulin (See, Patton, J. S. & Byron, *Nature Reviews Drug Discovery* 6, 67-74 (2007); White, S. S. et al., *Diabetes technology & therapeutics* 7 (6), 896-906 (2005); and Pearson, J., *Drug Delivery Report Spring/Summer*, 19-21 (2006)). Although it was withdrawn from the market by the manufacturer a year after launch, patient satisfaction with inhaled insulin was quite high compared with injections, particularly among patients with needle anxiety (Brunton, S., *Am J Med*, 121 (6 Suppl), S35-41 (2008)).

A recent study comparing the effects of the inhaled GH and the subcutaneous GH in children with the GH deficiency was encouraging and promising. They reported that the inhaled GH was well tolerated and resulted in dose-dependent increases in serum GH and IGF-I levels. No significant changes in pulmonary functions were observed. However, the mean relative bioavailability for the inhaled GH was only 3.5% and the mean relative biopotency, based on IGF-I response, was 5.5% (Walvoord, E. C. et al., *J Clin Endocrinol Metab* 94 (6), 2052-2059 (2009)). These results suggest that a larger amount of GH will be needed in order to achieve the same clinical effects as subcutaneously injected GH.

Meanwhile, the N-methyl-D-aspartate class of glutamate (NMDA) receptors is involved in several physiological and pathophysiological processes, including synaptic plasticity, ischemia, neurodegeneration, and convulsions (Furukawa, H. et al. 2005, *Nature* 438: 185-192). And the NMDA receptor, are thought to have an important role in the induction of long-term potentiation (LTP), which is believed to be one of the required mechanisms for the development of memory at a synaptic level. The NMDA receptor subunits NR1 and NR2A-D have important roles in brain plasticity and behavior. NR1, NR2A and NR2B have been specially linked with hippocampal synaptic plasticity and learning parameters. This NMDA receptor-PSD-95 complex is associated with the induction of LTP and synaptic plasticity in the dentate gyrus area of the hippocampus.

Further, NMDA receptor hypofunction is implicated in a range of cognitive and behavioral functions of animals and humans (see, Cao, X. et al., *Eur J Neurosci* 25 (6), 1815-1822 (2007); and Ng D, P. G., *PLoS Biol* 7 (2), 41 (2009)). There is strong evidence that the NMDA receptors preferentially affect the neural mechanisms regulating the efficiency of encoding and consolidation into longer-term memorystorage (Clark, R. E., *Hippocampus* 15 (2), 260-272 (2005)). Severe NMDA receptor hypofunction can produce clinical syndromes including core features of psychosis, schizophrenia as well as dissociation (Li F, T. J., *N Engl J Med.* 361 (3), 302-303 (2009)).

The present inventors have endeavored to develop a safe and effective inhalable formulation comprising growth hormone (GH) and have found that said formulation can be effectively used in the treatment of an NMDA receptor hypofunction-related disease.

SUMMARY OF THE INVENTION

Accordingly, it is an object of the present invention to provide a use of an inhalable powder formulation comprising growth hormone (GH) for preventing or treating an NMDA receptor hypofunction-related disease.

It is another object of the present invention to provide a method for preventing or treating an NMDA receptor hypofunction-related disease in a subject by employing said inhalable powder formulation.

It is a further object of the present invention to provide an inhalable powder formulation for preventing or treating an NMDA receptor hypofunction-related disease comprising growth hormone (GH) as an active ingredient.

In accordance with one aspect of the present invention, there is provided a use of an inhalable powder formulation comprising growth hormone (GH) as an active ingredient for preventing or treating an NMDA receptor hypofunction-related disease.

In accordance with another aspect of the present invention, there is provided a method for preventing or treating an NMDA receptor hypofunction-related disease in a subject, which comprises administering a therapeutically effective amount of an inhalable powder formulation comprising growth hormone (GH) to the subject in need thereof.

In accordance with a further aspect of the present invention, there is provided an inhalable powder formulation for preventing or treating an NMDA receptor hypofunction-related disease comprising growth hormone (GH) as an active ingredient.

BRIEF DESCRIPTION OF THE DRAWINGS

The above and other objects and features of the present invention will become apparent from the following description of the invention, when taken in conjunction with the accompanying drawings, which respectively show:

FIG. 2B (# (SC vs INH 200): P=0.260; ## (INH 200 vs INH 600): P=0.068; and * (SC vs INH 600): P=0.005 (Anova, post hoc LSD));

FIG. 2E (#: P=0.569 using Kruskal Wallis test));

FIG. 4C: GH plasma concentration-time curves following IV injection, SC injection; and intratracheal insufflation of GH dry powder, INH 200.

DETAILED DESCRIPTION OF THE INVENTION

Figure 1A:
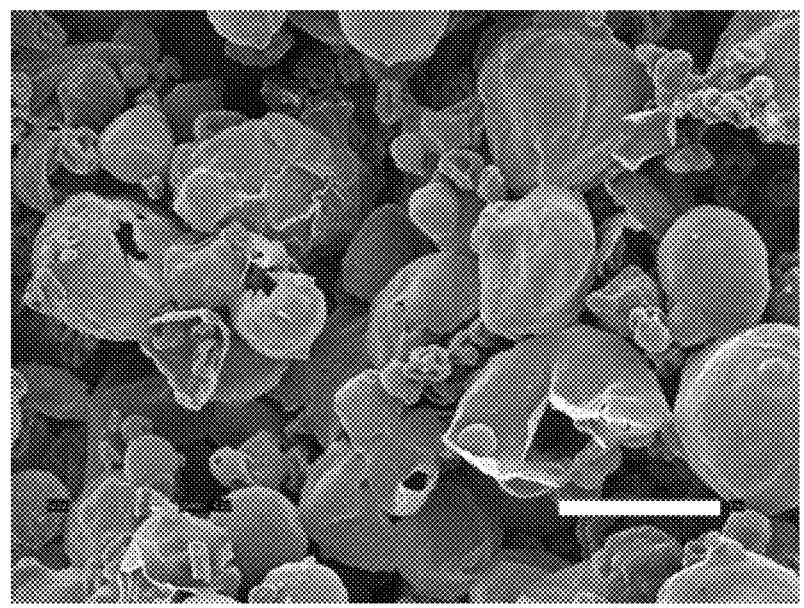
FIG. 1A: Scanning electron microscopic images of spray-dried powder particles (5000×. Scale bar=10 μm)

In the present invention, there is provided a use of an inhalable powder formulation comprising growth hormone (GH) as an active ingredient for preventing or treating an NMDA receptor hypofunction-related disease.

Further, a method for preventing or treating an NMDA receptor hypofunction-related disease in a subject, which comprises administering a therapeutically effective amount of an inhalable powder formulation comprising growth hormone (GH) to the subject in need thereof, is also provided.

In addition, there is provided an inhalable powder formulation for preventing or treating an NMDA receptor hypofunction-related disease comprising growth hormone (GH) as an active ingredient.

The term "an NMDA receptor hypofunction-related disease" as used herein refers to any disease or disorder caused by the hypofunction of an NMDA receptor, for instance, NMDA receptor 1 (NR1), NMDA receptor 2A (NR2A) and NMDA receptor 2B (NR2B), due to age related process or the condition induced in the human or animal brain by an NMDA antagonist drug, might also be viewed as a model for a disease mechanism which could explain the symptoms and natural course of schizophrenia. The disease mechanism itself might involve dysfunction of the NMDA receptor or downstream effects that can be modeled by blocking NMDA receptors. One typical consequence of blocking NMDA receptors is excessive release of Glu and acetylcholine in the cerebral cortex. It has been proposed that this excessive release of excitatory transmitters and consequent overstimulation of postsynaptic neurons might explain the cognitive and behavioral disturbances associated with the NMDA receptor hypofunction state. It is assumed that both genetic and nongenetic factors can contribute to the NMDA receptor hypofunction state and that this state is instilled in the brain early in life as a latent condition with the potential to erupt and trigger psychotic manifestations in adulthood but not usually in pre-adult life.

Such diseases may include schizophrenia; schizophrenia-like symptoms including cognitive impairments; Alzheimer's disease; age-related decreases in memory and learning; drug-induced NMDA receptor hypofunction; NMDA antagonist-induced psychotic symptoms or cognitive impairments; huntington disease; and chronic alcoholics.

The term "powder" or "powdered" refers to a formulation that consists of finely dispersed solid particles that are relatively free flowing and capable of being dispersed in an inhalation device and subsequently inhaled by a subject so that the particles reach the lungs to permit penetration into the alveoli.

The term "dispersibility" means the degree to which a powder formulation can be dispersed (i.e. suspended) in a current of air so that the dispersed particles can be respired or inhaled into the lungs of a subject. For example, a powder formulation that is only 10% dispersible means that only 10% of the mass of finely-divided particles making up the formulation can be suspended for oral inhalation into the lungs; 50% dispersibility means that 50% of the mass can be suspended.

The term "therapeutically effective amount" is the amount of growth hormone present in the powder formulation that is needed to provide the desired level of the growth hormone to a subject to be treated to give the anticipated therapeutic response.

The term "pharmaceutically acceptable" refers that an excipient, a carrier or other additives used in the formulation can be taken into the lungs with no significant adverse toxicological effects on the lungs.

The growth hormone used in the formulation may be any of mammalian growth hormones, while human growth hormone is preferred. The growth hormone may be wild-type ones or genetic recombination products.

The formulation may contain between 0.01 mg/kg and 10 mg/kg, preferably, between 0.05 mg/kg and 0.5 mg/kg of growth hormone.

The inhalable powder formulation used in the present invention may comprise a suitable pharmaceutically-acceptable excipient in addition to a therapeutically effective amount of growth hormone. Such excipients must be physiologically acceptable when used in administration by the aerial pathways.

The excipients which satisfy this requirement will be selected from a group consisting of monosaccharides such as glucose and arabinose; disaccharides such as lactose, saccharose and maltose; polysaccharides such as sorbitol, mannitol and xylitol; salts such as sodium chloride and calcium carbonate; sodium bicarbonate; amino acids; peptides; polymers; lipids; and a mixture thereof.

Preferably, the excipients are mono-, di- or polysaccharides, among which, lactose is most preferred.

The formulation may contain between 0.01 mg/kg and 10 mg/kg, preferably, between 0.05 mg/kg and 0.5 mg/kg of excipient.

Surfactants, such as dipalmitoyl phosphatidylcholine (DPPC) may be incorporated to the formulation to further improve powder flow, aerosol dispersion and lung deposition.

The formulation may contain between 0.01 mg/kg and 10 mg/kg, preferably, between 0.05 mg/kg and 0.5 mg/kg of surfactant.

Optionally, a further particulate active ingredient suitable for inhalation therapy may be incorporated into the formulation such as a corticosteroid (e.g., fluticasone propionate) or a bronchodilator (e.g., salmeterol or albuterol or a salt thereof).

It will be appreciated that the formulations according to the present invention may contain minor amounts of other additives, e.g., taste masking agents or sweeteners.

Further, the formulation of the present invention may be formulated so as to provide quick, sustained or delayed release of the active ingredient after administration to a patient by employing any of the procedures well known in the art.

On exemplary inhalable powder formulation may comprise human growth hormone (hGH), lactose and dipalmitoyl phosphatidylcholine (DPPC) in the ratio of 1:0.5-1.5: 1-5 by weight, preferably, 1:1:3 by weight.

The inhalable powder formulation may be prepared by spray drying process as described in the literature (Bosquillon et al., *J. Control. Rel.* 96 (2004): 233-244)).

For instance, the inhalable powder formulation comprising growth hormone, DPPC and lactose may be prepared by the steps of (1) combining DPPC dissolved in a solvent (e.g., ethanol) with an aqueous solution containing GH and lactose to obtain an aqueous mixture; and (2) subjecting the aqueous mixture to a spray drying process to obtain an inhalable powder formulation.

The inhalable powder formulation can be advantageously delivered by dry powder inhaler or by metered dose inhaler. For delivery of dry inhalable powder, growth hormone is milled, precipitated, spray dried or otherwise processed to particle sizes (mass median aerodynamic diameter; MMAD) between about 1 and 10 μm, preferably between about 1 and 5 μm.

The dry powder formulation is practical and convenient for ambulatory use because it does not require dilution or other handling, it has an extended shelf-life and storage stability and the dry powder inhalation delivery devices are portable and do not require an air compressor needed by aerosol nebulizers.

All techniques suitable for preparation of dry inhalable powders and any and all improvements thereof as well as any dry powder inhaler are intended to be within the scope of the invention.

In the method for preventing or treating an NMDA receptor hypofunction-related disease, the subject may be a mammal comprising a human, a mouse, a rat, a sheep and a rabbit, preferably, a human.

The inhalable formulation comprising GH is efficaciously delivered to a patient's endobronchial space of airways by inhalation of a dry powder.

The formulation of the present invention may be delivered from a unit dosage receptacle containing an amount that will be sufficient to provide the desired physiological effect upon inhalation by a subject in need thereof. The amount may be dispersed in a chamber (or insufflator) that has an internal volume sufficient to capture substantially all of the powder dispersion resulting from the unit dosage receptacle.

The effective daily dose of the growth hormone for the treatment of NMDA receptor hypofunction-related diseases may range from about 0.01 to 10 mg/kg, preferably 0.05 to 0.5 mg/kg body weight when administered in the form of the inhalable formulation, and can be administered in a single dose or in divided doses. However, it should be understood that the amount of the active ingredient actually administered ought to be determined in light of various relevant factors including the condition to be treated, the age and weight of the individual patient, and the severity of the patient's symptom; and, therefore, the above dose should not be intended to limit the scope of the invention in any way.

In the preferred embodiments of the subject invention, the bioactivity of the GH in the formulation was evaluated by measuring the weight gain; the increase of the tibial growth panel width; the improvement of learning/memory acquisition; and the NR1, NR2A and NR2B expression.

The oral inhalation of the formulation comprising GH generated a remarkable treatment effect in weight gain (FIGS. 2A and 2B), the increase of the tibial growth panel width (FIG. 2C) and the improvement of learning/memory acquisition (FIGS. 3A and 4A), such remarkable effect cannot be achieved by any other mode of administration (intravenous (IV) or subcutaneous (SC) injection). Also, high levels of NR1, NR2A and NR2B were expressed in the brains of the experimental animals administered with the inhalable formulation comprising GH (FIGS. 3B and 4B).

Thus, the inhalation of growth hormone permits an administration of small yet effective amount of growth hormone directly into lungs and exhibits more superior effect than other previously known methods used for the delivery of growth hormone in the treatment of the NMDA receptor hypofunction-related diseases.

The present invention thus provides an efficacious, safe, nonirritating and physiologically compatible inhalable growth hormone formulation suitable for the treatment of NMDA receptor hypofunction-related diseases.

In addition, the present invention provides an inhalable powder formulation for preventing or treating an NMDA receptor hypofunction-related disease comprising growth hormone (GH) as an active ingredient.

The following Examples are intended to further illustrate the present invention without limiting its scope.

Example 1: Preparation of Spray-Dried rhGH Powder

Human growth hormone (GH; Growtropin®, Dong-A Pharmaceutical co., Ltd (Yongin-si, Korea) was first purified by ultrafiltration (MWCO: 10,000) to remove the inactive ingredients included in the solution form of GH. Dry powder containing GH was produced by the LabPlant SD-05 spray dryer (Lab-Plant Ltd, Huddersfield, UK). Dry powder containing bovine serum albumin (BSA; Sigma) instead of GH was also prepared as a negative control.

In both cases, protein (GH or BSA), lactose (Mallinckrodt (Paris, Ky., USA)), and dipalmitoylphosphatidylcholine (DPPC; Lipoid GmbH (Ludwigshafen, Germany)) were dissolved in the weight ratio of 1:1:3 in 70% ethanol to make a 2 mg/mL feed solution. Briefly, DPPC was first dissolved in 95% ethanol and then combined with an aqueous solution containing GH (or BSA) and lactose. The feed solution was maintained at 40° C. and constantly stirred during the spray-drying process. The solution was introduced to the spray-dryer at a rate of 17 mL/min and atomized instantly through a 1-mm orifice nozzle using compressed air. The resulting solution heated at 120 to 150° C. of an inlet temperature, to obtain the inventive spray-dried rhGH powder (hereinafter, referred to as "GH powder").

Example 2: Characterization of Spray-Dried rhGH Powder

To analyze the characteristics of spray-dried rhGH powder prepared in Example 1, three tests were performed.
2-1. Anderson Cascade Impactor (ACI)

Aerodynamic particle size distribution was determined using an eight-stage Mark II.

10 mg of the GH Powder obtained in Example 1 samples was manually loaded into hard gelatin capsules (size 3), which were put in a Rotahaler and split-open to release the particles. Glass fiber filters were placed on the ACI stages to prevent particle bounce or re-entrainment (Vanbever, R. et al., *Pharmaceutical research* V16 (11), 1735 (1999)). Each set of powder was drawn through the induction port into the ACI operated at a flow rate of 28.3 L/min for 10 sec. The amount of particles deposited at individual impaction stage was determined by measuring the difference in weight of glass fiber filters (for the filter stage, pore size <1 μm, ThermoFisher; for all other stages, pore size 1 μm, Pall Corp.) placed on the stages. The effective cutoff aerodynamic diameters for each stage were: Stage 0 (9 μm); Stage 1 (5.8 μm); Stage 2 (4.7 μm); Stage 3 (3.3 μm); Stage 4 (2.1 μm); Stage 5 (1.1 μm); Stage 6 (0.65 μm); and Stage 7 (0.43 μm). The fine particle fraction (FPF) was defined as the amount of powder with an aerodynamic size <4.7 μm (particles deposited at stage 3 and lower) divided by the initial total powder loaded in the Rotahaler (10 mg, nominal dose). The cumulative mass of powder less than effective cutoff diameter as percent of total mass recovered in the ACI was plotted against the effective cutoff diameter. The mass median aerodynamic diameter (MMAD) was defined on this graph as the particle size at which the line crossed the 50th percentile.
2-2. Scanning Electron Microscopy The morphology of the spray-dried GH powder prepared in Example 1 was examined using scanning electron microscopy. The spray-dried GH powders were attached to specimen stubs using double-sided tape and sputter-coated with gold-palladium in the presence of argon gas using a Hummer I sputter coater (Anatech Ltd.). GH powders were imaged with a JEOL JSM-840 scanning electron microscope (JEOL USA, Inc.) using a 5 kV accelerating voltage, a 10 mm working distance, a 70 μm objective aperture, and a probe current of $6 \times 10^{-11}$ amps.

The results are shown in FIG. 1A (Scanning electron microscopic images of spray-dried particles (5000×. Scale bar=10 μm). As shown in FIG. 1A, the GH powder was spherical and hollow, which explains the smaller MMAD than the geometric diameter (~10 μm) observed by SEM. The control powder (containing BSA instead of GH) had similar aerodynamic properties.
2-3 Analysis of GH Recovered from Dry Powder To test the integrity of spray-dried GH, the protein was recovered from the powder and analyzed by the size-exclusion HPLC according to the assay method described in the U. S. Pharmacopeia.

5 mg of GH powder was accurately weighed, suspended in 1 ml phosphate buffered saline (PBS, pH 7.4), and incubated at 37° C. with constant stirring. At 1, 3, and 24 hours, the particle suspension was centrifuged at 8000 rpm for 5 min and 0.8 mL of supernatant was sampled for analysis. After each sampling, fresh PBS was replaced. The concentration of GH in the supernatant was determined using High Pressure Liquid Chromatography (HPLC 1100 series, Agilent Technologies, Palo Alto, Calif.) and a gel filtration column (TSK G3000SWXL (300×7.8 mm; particle size 5 μm)). The mobile phase was a mixture of 0.06M phosphate buffer and isopropyl alcohol in the ratio of 97:3 (v/v). The flow rate was 0.6 mL/min. 5 μL of each sample was injected into the pre-equilibrated column followed by 30 min of wash with the mobile phase. The UV detector was set at 214 nm. Retention time of rhGH was 17.6-17.7 min.

Figure 1B:
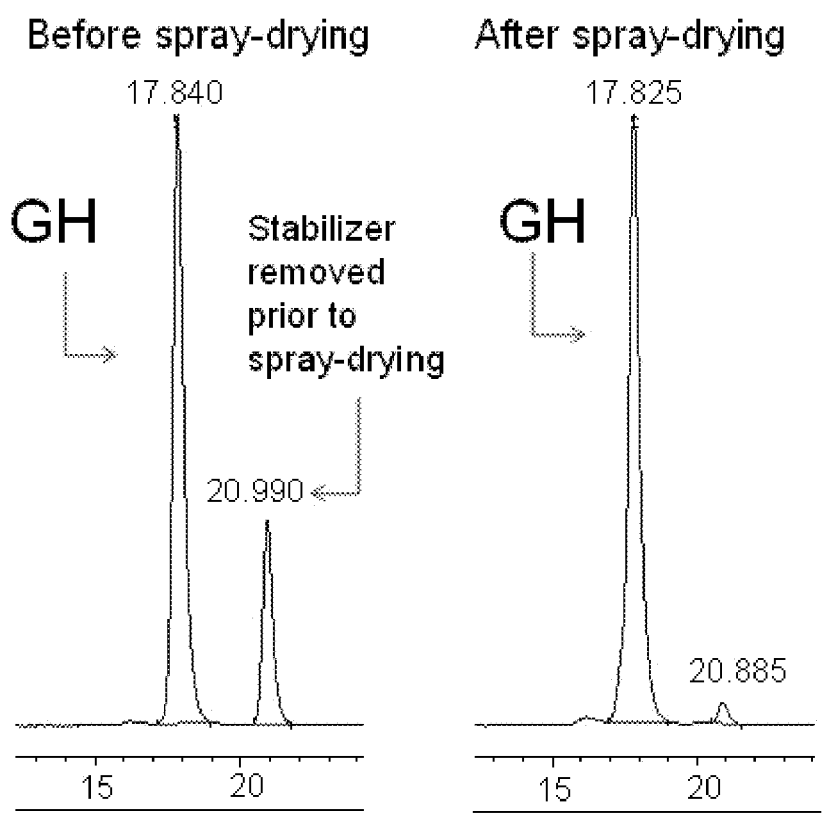
FIG. 1B: SEC-HPLC analysis of original GH prior to spray-drying (left) and GH recovered from the powder (right)

The results are shown in FIG. 1B (Original GH prior to spray-drying (left) vs. GH recovered from the powder (right)). Note that the additional peak in the original GH corresponds to the stabilizer included in the original GH solution, which was removed by ultrafiltration prior to the spray-drying.

As shown in FIG. 1B, The GH recovered from the powder was similar to that of original GH, indicating that the spray-drying process did not compromise the integrity of GH. The HPLC analysis revealed that 1 mg of powder contained 0.128±0.01 mg of GH. The powder was weighed based on this measurement to provide the desired dose of GH to the rats.

Test Example: Preparation of Test Animals and GH Administration for Efficacy and Safety Testing All animal experiments were performed with the approval of the Institutional Animal Care and Use Committee, Laboratory Animal Research Center, Samsung Biomedical Research Institute (Seoul, Korea). All procedures conformed to the international guidelines for the ethical use of laboratory animals, and efforts were made to minimize the number of animals used and to avoid any unnecessary suffering.

In statistical analysis, all results are expressed as mean±standard errors of the mean (S.E.M.). One-way analysis of variance (ANOVA) test and LSD test were performed to demonstrate statistical differences (p<0.05), using the software Sigma-stat for Windows (SPSS Inc., Chicago, Ill.).

Test Example 1: Weight Gain 5-week-old hypophysectomized (HYPDX) male Sprague Dawley rats (hypophysectomized at 4 weeks of age), weighing approximately 80-100 g, were purchased from Japan SLC, Inc. The rats were weighed during 7 days of acclimatization, and only those in good health and with constant weights (body weight change: <10%) were selected for the study. The rats were housed under standardized conditions (12-h light and 12-h dark cycle; lights switched off at 07:30 hours; temperature, 21-26° C.; and humidity, 40-60% RH). Food and drinking water were available ad libitum.

Rats (7 per group) were randomized by weight to 5 experimental groups as follows. For the efficacy and safety study, Animals in the SC group received subcutaneous injection of GH (200 µg/kg) daily. Animals in the INH 200 group received the GH powder (GH: 200 µg/kg) daily. Animals in the INH 600 group received the GH powder (600 µg/kg) daily. Two control groups were treated with saline and the control powder in the amounts equivalent to the GH solution in the SC group and the GH powder in the INH 200 group, respectively.

The GH powder was delivered directly into the trachea through a powder insufflator (Model DP-4; Penn-Century, Philadelphia, Pa.). First, the animals were anesthetized with ketamine (50 mg/kg) and xylazine (5 mg/kg) and placed ventral side up on a book stand and intubated using a 16-gauge 2-inch long IV indwelling cannula as an endotracheal tube. Dry powders containing GH or BSA prepared in Example 1 were loaded in the insufflator. The powder mass was quantified by weighing the device before and after loading the sample. The delivery tube of the insufflator was placed at the entry of the cannula, and the powders were then introduced to the lungs by supplying 1 mL of air contained in a syringe connected to the device. The animals were treated in this manner for 15 days, monitoring the weight gain during the first 10 days. Body weight was measured at 08:00 hours every day.

Then, the effect of inhaled GH (INH 200 and INH 600) on the weight gain varying the dose was investigated, and compared with those of the SC- and control groups. The results are shown in FIGS. 2A and 2B.

Figure 2A:
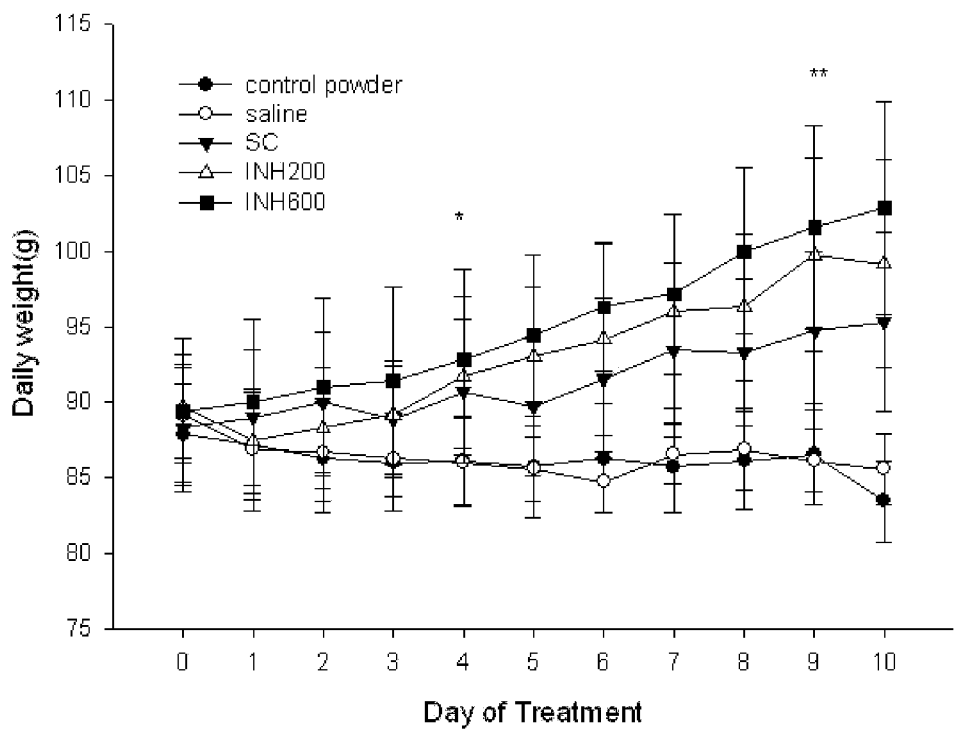
FIGS. 2A and 2B: the effects of GH on body weight of male hypophysectomized (HYPDX) rats (FIG. 2A (*: p=0.017, Anova; and ** (SC vs. INH 600): P=0.017, post hoc LSD)
Figure 3A:
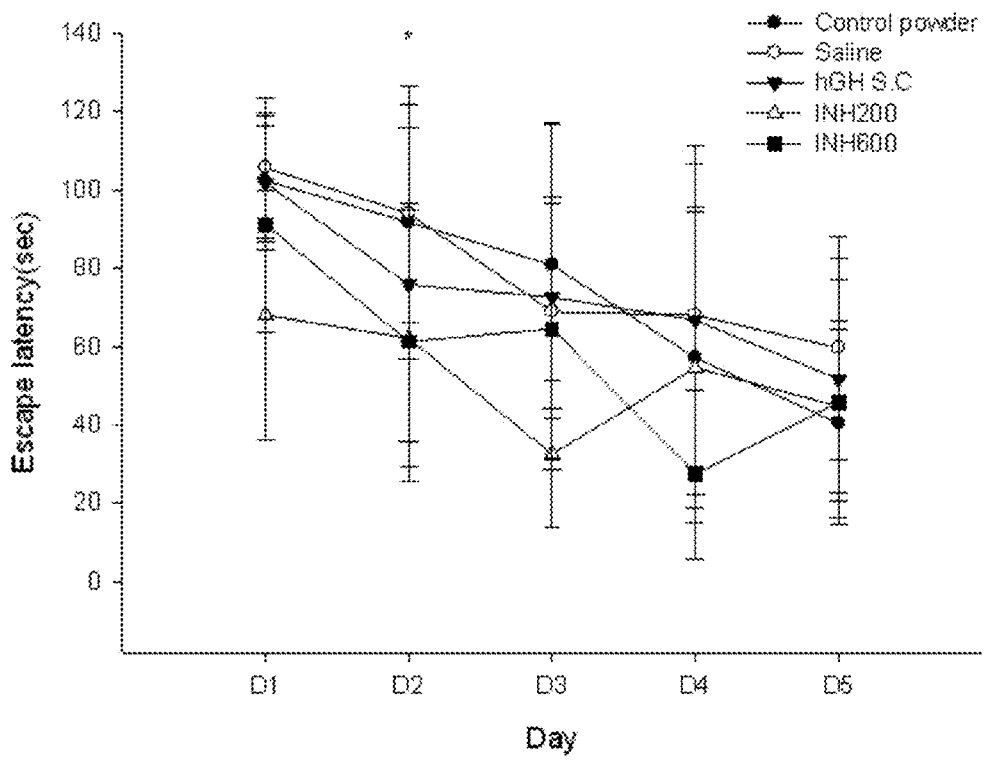
FIG. 3A: Effects of GH treatment of HYPDX rats on performance in the MWM test from experimental days 11 to 15 (*: P=0.033)
Figure 3B:
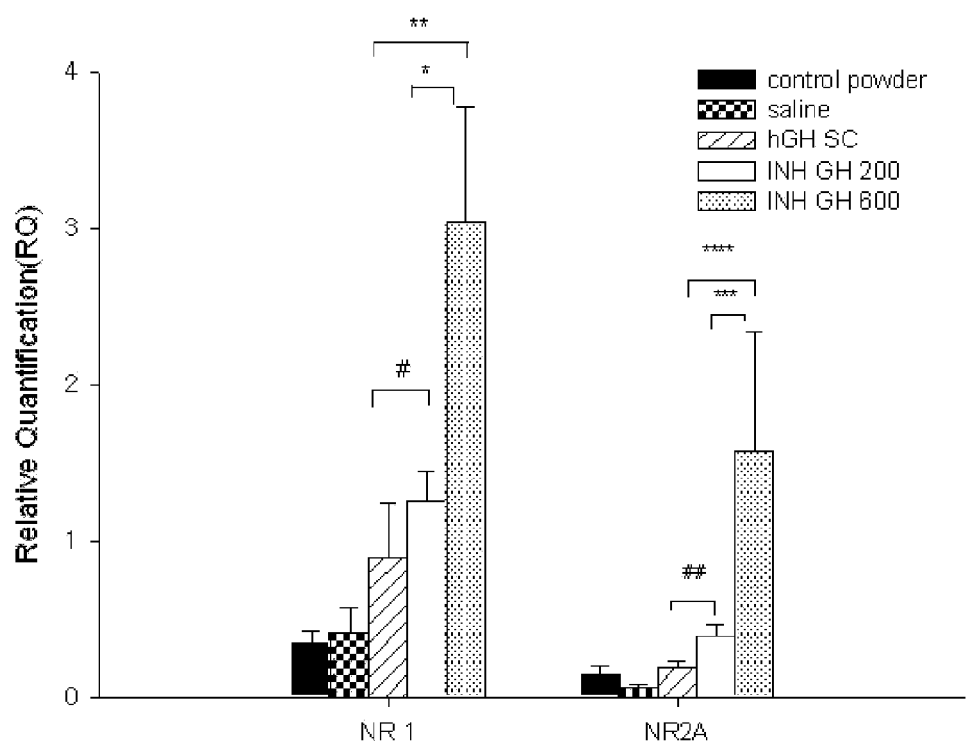
FIG. 3B: Expression level of NMDA receptors measured at 15 days after treatment (#: P=0.437; * P<0.001; : P<0.001; ##: P=0.592; *: P<0.001; and ****: P<0.001)

FIG. 2A shows changes in the mean values of weights of different treatment groups. Significant weight gains were observed both in the groups receiving subcutaneous injection (SC: 200 µg/kg/day) and inhalable GH powders (INH 200 and INH 600: 200 and 600 µg/kg/day, respectively) during the 10-day period. No difference was noted between INH 200 group and SC group.

Figure 2B:
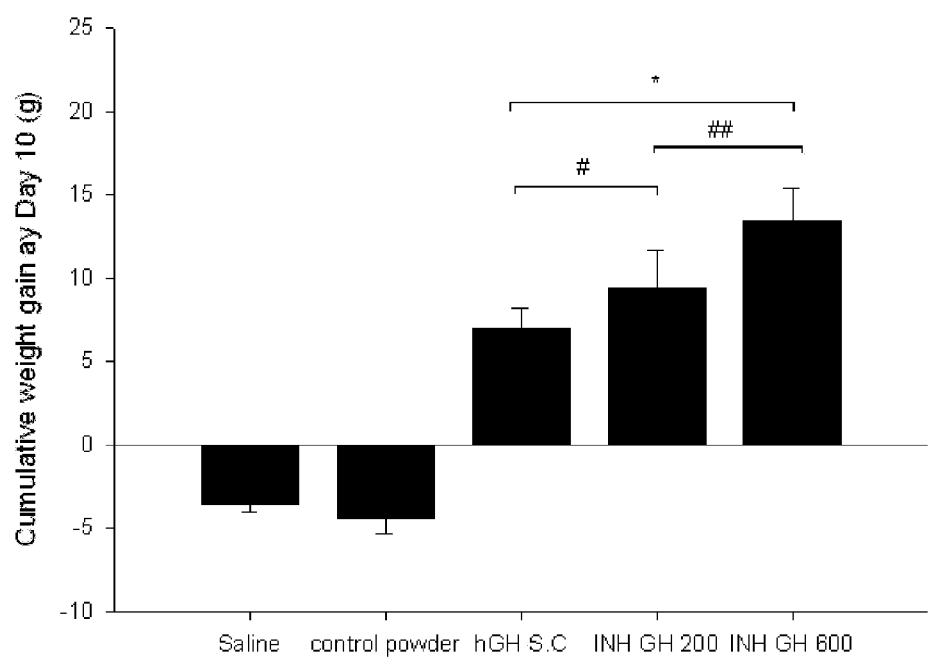

FIG. 2B shows net weight change in 10 days, the inhaled GH (INH 200, INH 600) resulted in rapid weight gain than the control powder or saline. While the weight gain by the inhaled GH was dose-dependent, the difference between INH 200 and INH 600 was not statistically significant (P=0.068).

Test Example 2: The Width of the Proximal Tibial Growth Plate

The effect of inhaled GH (INH 200 and INH 600) on the increase of tibial growth plate width was examined with varying the dose, and compared with those of the SC- and control groups.

Figure 2C:
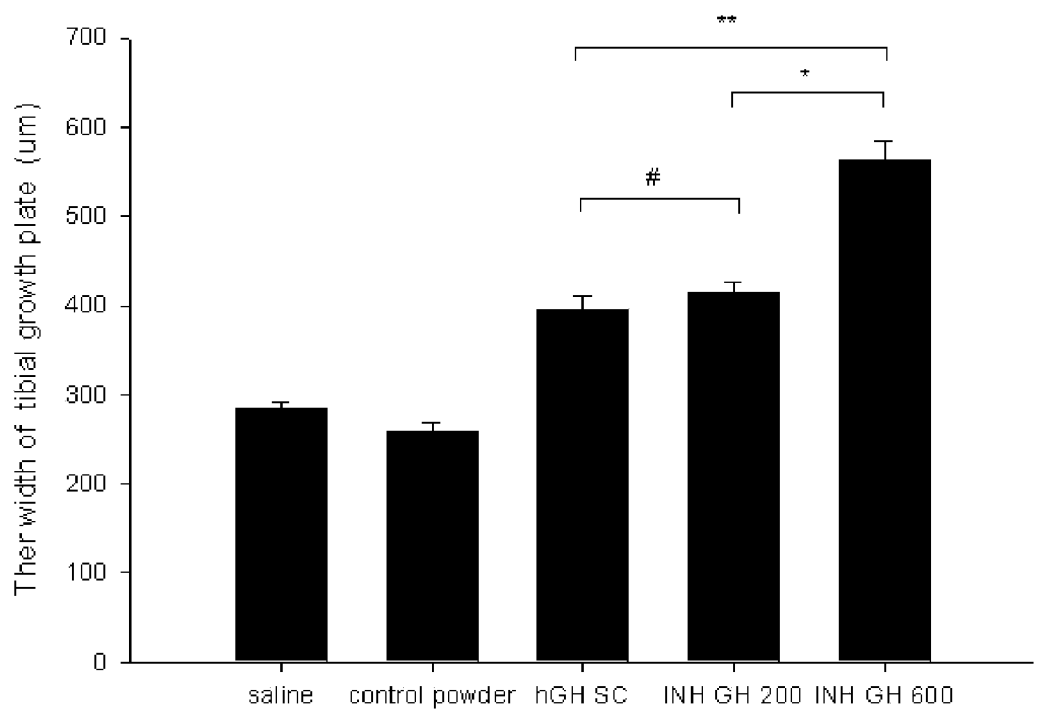
FIG. 2C: Width of tibial growth plate of male hypophysectomized rats after 15 days of treatments (#: P=0.247; *: P<0.001; and **: P<0.001)

On the 16$^{th}$ day, the animals were euthanized by $CO_2$. And their tibias were harvested and fixed in 10% neutral buffered formalin. The fixed tibias were split along the frontal plane at the proximal end. The tibias were processed for paraffin embedding, sectioned, and stained with hematoxylin & eosin. The measurement of the width of the proximal tibial growth plate was performed on the left tibia. Three measurements per section (medial, central, and lateral) were made at the magnification of 100× under a light microscope. The 3 measurements were averaged to determine the width of the proximal tibial growth plate, and the results are shown in FIG. 2C.

The increase of the width of tibial growth plate (FIG. 2C) showed the consistent trend as the weight gain, i.e, no difference was noted between INH 200 and SC group of the same dose (P=0.247), but INH 600 group showed more weight gain and tibial growth plate) than INH 200 group (P<0.001) or SC group (P<0.001).

Test Example 3: Lung Safety

Immediately after euthanasia, 1 mL of blood was drawn from the aorta. Arterial gas levels were immediately measured with blood gas analyzer (Rapidlab® 865)(FIG. 2F). The chest was then opened, the heart removed, and the trachea exposed and ligated with a 3-0 suture. The lungs were harvested and carefully trimmed of nonpulmonary tissue. Then left lung was weighed, and dried in an oven at 95° C. for 48 hours. The lung water content was estimated by calculating the ratio of the difference between the wet lung weight and the dry lung weight to the body weight (FIG. 2D) (Ichinose, M. et al., Intern Med 34 (1), 18-23 (1995)).

Then, the rat lung was harvested and fixed in 10% neutral buffered formalin. The lung were processed for paraffin embedding, sectioned, and stained with hematoxylin & eosin. The level of lung injury was scored according to a previously reported system (Chen, H. I., Yeh, et al., Crit Care Med 34 (3), 758-764 (2006); and Kao, S. J. et al., Chest 126 (2), 552-558 (2004)) with modification (FIG. 2E). The extents of lung edema and infiltration of leukocyte and other cells were scored in the 0 (not observed) to 3 (severe) scale. The scores for edema and cell filtration were then summed to a final score, ranging from 0 to 6. The examiner was blinded as to the identity of the specimen. These scores were compared with the data reported by the other authors.

Figure 2D:
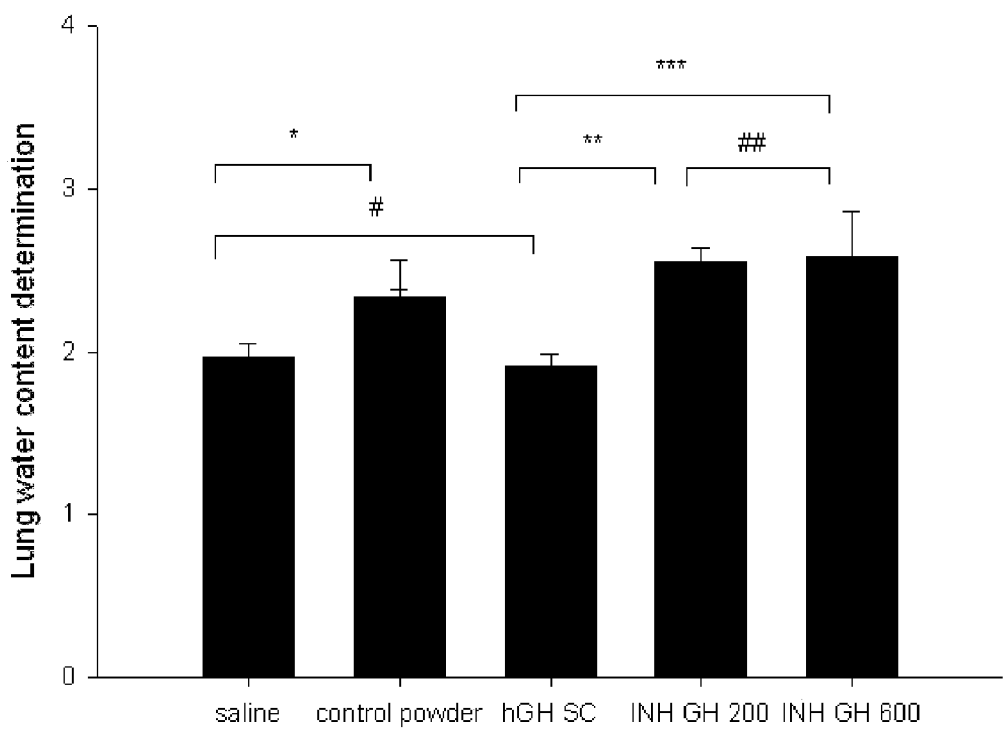
FIGS. 2D to 2F: Lung water content determination; Lung injury scores (edema formation and inflammatory cells infiltration) in isolated lungs; and Arterial blood gas analysis of male hypophysectomized rats, respectively (FIG. 2D (*: P=<0.001; # P=0.958; : P=0.004; ##: P=0.056; *: P<0.001)
Figure 2E:
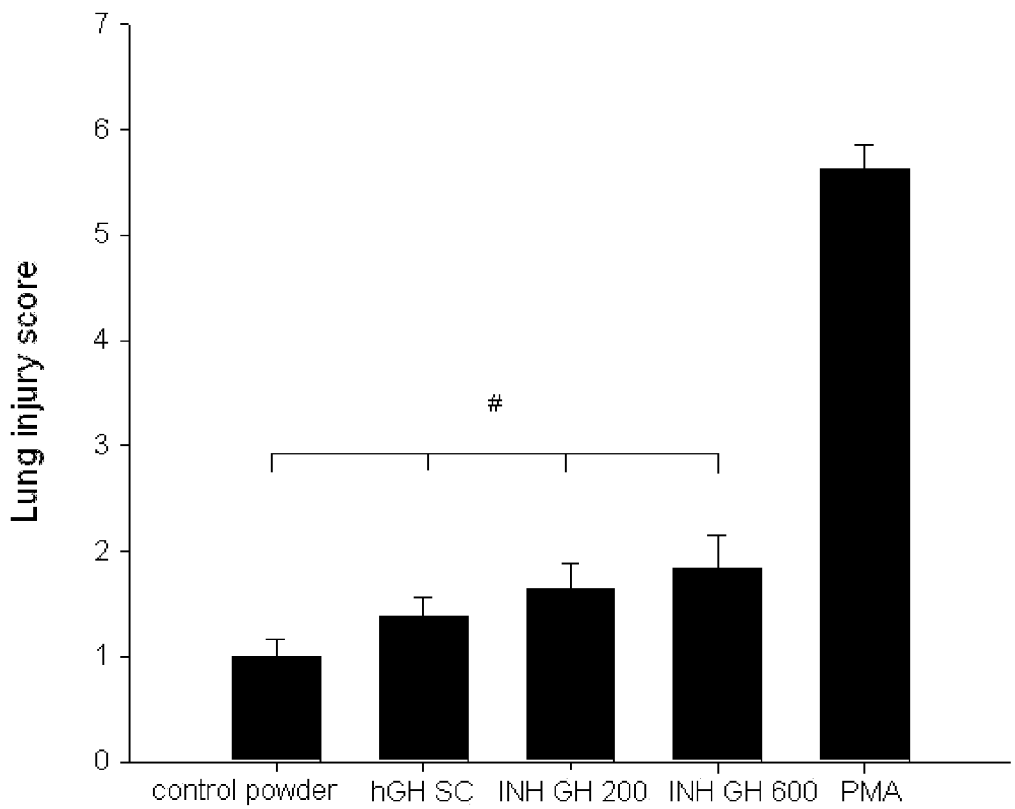
Figure 2F:
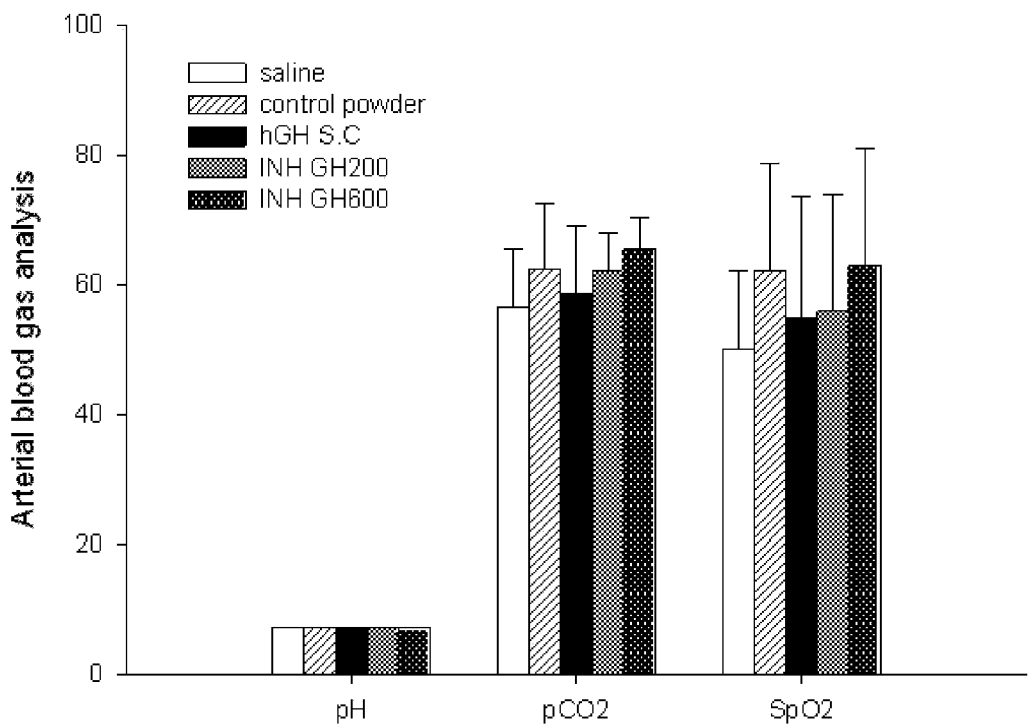

In the results, the safety of the inhaled GH, especially in the lungs, was evaluated by determination of the water content in the lungs (FIG. 2D). As shown in FIG. 2D, the water content in the lungs increased in all groups receiving inhalable powders including the control powder (P<0.001) as compared to the hGH subcutaneous injection group. There was no difference between the saline control group and the SC group (p=0.958). The Lung water content was deterninated by the following Equation 1:

$$\text{Lung water content} = (\text{the wet lung weight (mg)} - \text{the dry lung weight (mg)})/\text{body weight (g)} \times 100 \quad \text{<Equation 1>}$$

Also, Lung injury scores (edema formation and inflammatory cells infiltration) and analysis of the arterial blood gas (analysis of pH, $pCO_2$ (mmHg) and $sO_2$ (%)) in isolated lungs were determined using Kruskal Wallis test and Anova test, respectively. And the results are shown in FIGS. 2E and 2F. There was no difference between the groups.

Test Example 4: Learning/Memory Acquisition

To evaluate the improvement of the memory and learning acquisition in the animals receiving GH via different routes of administration, two tests were performed from the 11$^{th}$ day after initiation of the treatment: (i) the escape latency in Morris Water Maze (MWM) spatial reference memory task and (ii) the expression level of the subunits of NMDA receptors in the hippocampus of the animals that had completed the MWM test.

4-1 Morris Water Maze (MWM) Performance Test (Escape Latency)

The MWM performance test began on experimental day 11, and the test was continued for 5 consecutive days. The MWM test evaluates spatial learning and memory by measuring the capacity of animals to rescue themselves in a pool of water by reaching a hidden goal platform. The MWM test was conducted in a circular water-maze tank (157 cm diameter×60 cm height) filled with the non-transparent, dilute milk solution (temperature, 24±1° C.). A transparent Plexiglas platform (10 cm diameter×47 cm height) was submerged 3 cm below the water surface and placed in the one of the quadrants. The maze was located in the center of a well-lit room and was surrounded by black curtains (placed at 50 cm from the pool periphery) that contained 4 distinct external visual cues. The swimming path of each rat was monitored by an overhead video camera connected to a personal computer and analyzed by an automated tracking system (Smart v.20®; Panlab SL, Barcelona, Spain).

During the MWM test, the animals were required to locate the hidden platform, which remained in the same position, in relation to the external visual cues. One test session, which consisted of 3 trials, was carried out daily. In each trial, the rat was placed in the water facing the maze wall in one of the 3 quadrants except for the target quadrant containing a hidden platform. The order of entry into each quadrant was randomized daily. Each trial ended once the animals found the platform. If the rats were unable to find the platform within 90 sec, they were guided toward it by the experimenter. Once they have found or been placed on the platform, the rats were allowed to stay on it for 30 s. Subsequently, the rat was wiped dry with towel and positioned at a different start point for the next trial. At the end of a session, the rat was wiped dry with towel and returned to the home cage. In each trial, the time taken for the rat to reach the platform (escape latency in seconds), the length of the swim path (distance in centimeters), and the swimming speed (centimeters/second) were measured. For recovery from the fatigue from the MWM test, the daily GH administration was continued during the test period.

On day 15, probe trials were conducted at 2 hrs after completion of the final MWM test to evaluate spatial bias. The rats were released from the opposite quadrant from the one platform used to be located in and were allowed to swim for 60 sec in the absence of the platform. The percentage of time that the rats spent in the area that used to be occupied by the platform during the training period was measured. Since rats are nocturnal animals, all MWM tests were performed during the dark cycle. Effects of GH treatment of HYPDX rats on performance in the MWM test from experimental days 11 to 15, among the groups, using Anova and LSD post hoc test. Data were represented as the means±SEM (n=6). The results are shown in FIG. 3A. In the MWM test, the decrease in the escape latency at day 2 indicates better memory and learning ability. As shown in FIG. 3A, the INH groups showed significant improvement in the escape latency especially on the $2^{nd}$ day after initiation of the MWM test, while the SC group did not showed significant improvement. After 5 days of MWM test, all the animals were eventually accustomed to this test and showed the shortened escape latency.

4-2 Gene Expression in the Hippocampus Tissues

Upon completion of the MWM test, the animals were sacrificed to obtain the hippocampus and the expressions of NMDA receptor 1 (NR1) and NMDA receptor 2A (NR2A), which are known to be increased during memory/learning were determined. Expression level of NMDA receptors measured at 15 days after treatment.

After euthanasia, rat hippocampus tissue was isolated and soaked in TRIzol reagent (Invitrogen, Carlsbad, Calif.). The tissue was homogenized, and total RNA was isolated according to the manufacturer's protocols. The cDNAs were synthesized by SuperSciprt III reverse transcriptase (Invitrogen). Real-time polymerase chain reaction was performed to quantify the mRNA levels of NMDA receptor subunits and AMPA using an ABI PRISM 7900HT system and TaqMan gene expression assays (Applied Biosystems, Foster City, Calif.).

NR1 (Rn01436030_m1), NR2A (Rn00561342_m1), NR2B (RN00561352_m1), AMPA (Rn00691897_g1), and GAPDH (Rn01462662_g1, as the endogenous control) were labeled with FAM. The mRNA levels were expressed relative to the level of GAPDH. The 2-AACT method was used to analyze the data using SDS2.3 software (Applied Biosystems).

As shown in FIG. 3B, the expression levels of NMDA receptors increased significantly, particularly in the INH 600 groups. Of note, ketamine used for anesthesia is known to have negative effects on the memory/learning process negatively (Thompson, D. M. et al., *Pharmacol Biochem Behav* 26 (2), 401-405 (1987); and Frederick, D. L. et al., *Pharmacol Biochem Behav* 52 (4), 789-797 (1995)); however, since all animals involved in this experiment were anesthetized in the same manner, the influence ketamine anesthesia in the MWM test should be assumed minimal.

4-3 Improvement of Escape Latency and the Elevated Level of Expression of NR1 and NR2B in Inhalation Group Compared to the Intravenous Group at Day 2 and Day 5

To confirm that the effect of GH on the memory/learning process and recruitment of NMDA receptor subunits was dependent on the routes of administration and the dose, the effects of 3 routes of administration, i.e., IV (intravenous) injection, SC injection, and inhalation (all delivering 200 μg/kg/day), on the escape latency in the MWM test and the expression levels of NMDA receptors and AMPA receptor was examined.

Figure 4A:
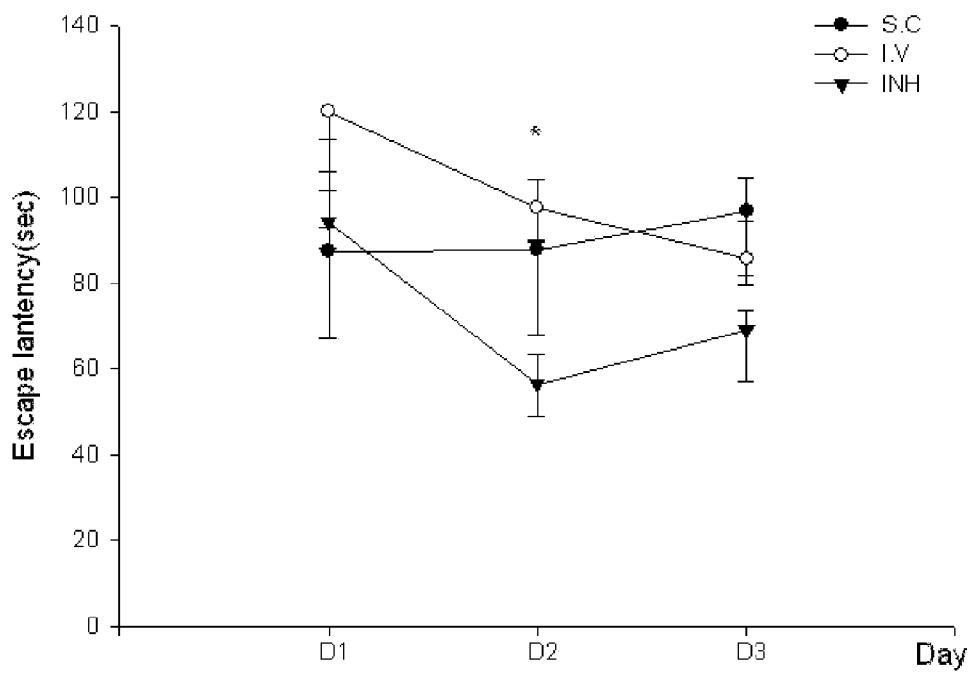
FIG. 4A: Effects of GH delivered by different routes on the performance of HYPDX rats in the MWM test (Upper panel (* P=0.031); and Lower panel (* P=0.086,  P=0.325, and * P=0.011)
Figure 4A:
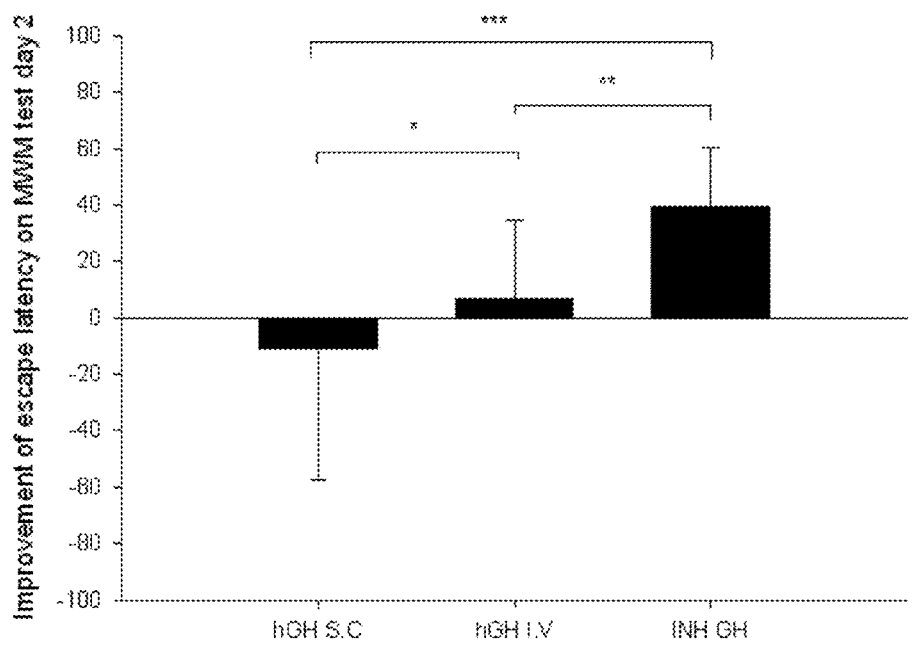
Figure 4B:
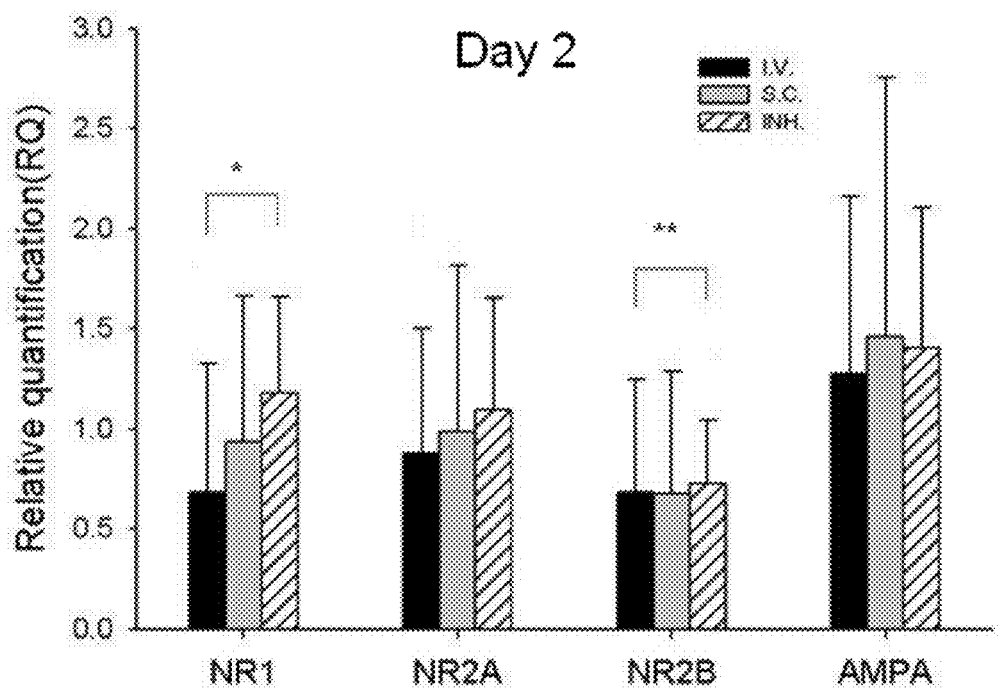
FIG. 4B: Expression of NMDA receptors and AMPA receptor (*: P=0.03; **: P=0.027; #: P=0.027; ##: P=0.027; student t-test)
Figure 4B:
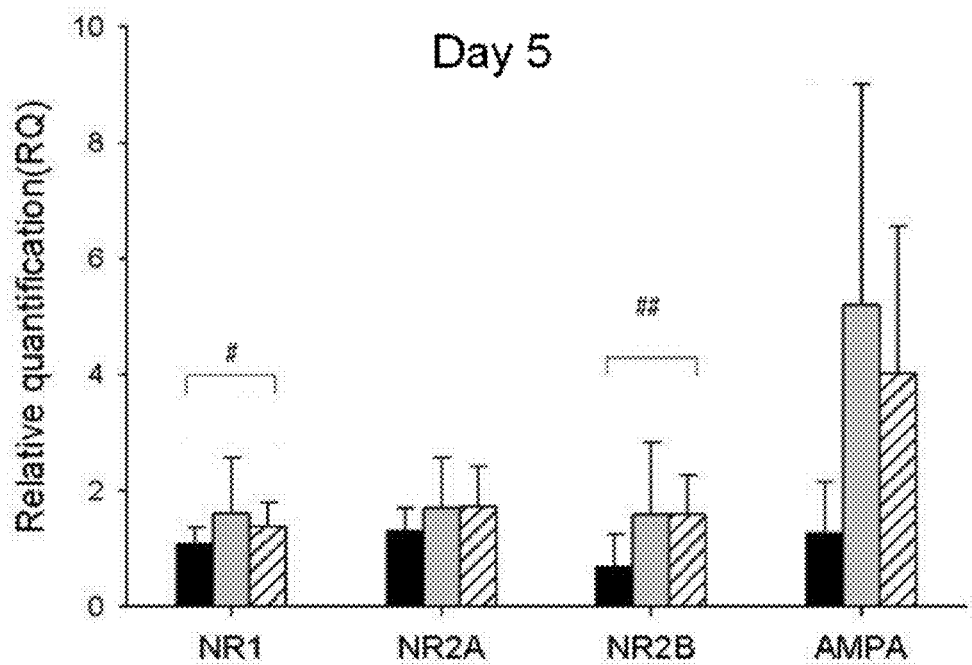

The results determined by using Anova and LSD post hoc test showed that the improvement of the escape latency was the most obvious in the inhalation (INH 200) group (FIG. 4A). In FIG. 4A, Upper panel showed effects of GH delivered by different routes on the performance of HYPDX rats in the MWM test. At Day 2, escape latency of inhalation group was the shortest. And Lower panel showed improvement of escape latency on day 2 of MWM test (escape latency of $1^{st}$ day-2nd day).

Also, the results of expression of NMDA receptors and AMPA receptor are shown in FIG. 4B. As shown in FIG. 4B, the expression levels of NR1 and NR2B was significantly higher in the INH 200 group compared to the IV group at day 2 (upper panel) and day 5 (lower panel), consistent with the improvement of the escape latency.

Test Example 5: Pharmacokinetic Studies

The animals were anesthetized with ketamine (70 mg/kg) and xylazine (7 mg/kg), and catheters for blood sampling and intravenous injection were implanted in the jugular veins of rats. The rats then received a GH dose by the intratracheal insufflation of a GH powder (INH 200), intravenous (IV) or subcutaneous (SC) injection. The amounts of powder and solution were adjusted according to the rat weight to provide 200 μg/kg of GH for all animals. The GH powder was delivered directly into the trachea through a powder insufflator as described in Test Example 1.

Blood samples were collected from the jugular vein and placed in heparin-treated tubes. The first sampling was performed just before the administration of GH (time "0"). Subsequently, 12 blood samples (200 μL per sampling) were collected over 4 h (IV injection; every 20 mins), 5 h (powder insufflation; every 25 mins) or 7 h (SC injection; every 35 mins). The animals received an equivalent volume of sodium chloride 0.9% w/v to compensate for the decrease in blood volume. The GH concentration in the serum was measured using the ImmunoRadiometric assay (IRMA, Dia-Sorin, Saluggia, Italy), which was specific to human GH (not cross-reactive with rat GH). The detection range of the immunoassay was 0.5-50 ng/mL, and the inter-assay relative standard deviation was 5.2%. Serum samples were assayed in duplicate after proper dilution. The rats were euthanized 15 days after the treatment for determination of the gene expression levels.

The pharmacokinetic data is shown in FIG. 4C. GH plasma concentration vs time curves following IV injection (triangles; n=8), SC injection (closed circles; n=7); and intratacheal insufflation of GH dry powder, INH 200 (open circles; n=8).

The present invention shows that the biological responses and pharmacokinetics of GH vary with the route of administration in the hypophysectomized rat model. The inhaled GH was more effective in promoting the weight gain and growth of the tibial growth plate than the GH of equivalent dose delivered subcutaneously. Except for the modest increase in the water content in the lungs, the inhaled GH showed comparable histological responses and lung functions to those of the subcutaneous GH. In addition, the inhaled GH administration reduced the escape latency in the hypophysectomized rat model and increased the levels of NMDA receptor subunits expression.

In conclusion, the same amount dose of inhalable form of growth hormone was as effective and safe as an injectable form for growth promotion and was more efficient in expressing receptors of NR1 and NR2B in the brain. An inhalable form of growth hormone is a promising route of administration not only for the promotion of growth but also for clinical applications in several disorders, where the expression of NMDA receptor is decreased.

While the invention has been described with respect to the above specific embodiments, it should be recognized that various modifications and changes may be made to the invention by those skilled in the art which also fall within the scope of the invention as defined by the appended claims.

What is claimed is:

1. A method for treating an N-methyl-D-aspartate (NMDA) receptor hypofunction-related disease, which comprises administering a therapeutically effective amount of an inhalable powder formulation comprising growth hormone to a subject in need thereof, wherein the NMDA receptor hypofunction-related disease is schizophrenia;

wherein the therapeutically effective amount is 0.05-0.5 mg/kg body weight per day;

wherein the inhalable powder formulation further comprises a corticosteroid; and wherein the inhalable powder formulation comprises the growth hormone in an amount of 0.128±0.01 mg per g of the inhalable powder formulation.

2. The method of claim 1, wherein the inhalable powder formulation further comprises a pharmaceutically acceptable excipient.

3. The method of claim 2, wherein the pharmaceutically acceptable excipient is selected from the group consisting of a monosaccharide; a disaccharide; a polysaccharide; sodium chloride; calcium carbonate; sodium bicarbonate; an amino acid; a peptide; a polymer; a lipid; and a mixture thereof.

4. The method of claim 1, wherein the inhalable powder formulation comprises growth hormone, lactose, and dipalmitoyl phosphatidylcholine.

5. The method of claim 4, wherein the inhalable powder formulation comprises human growth hormone, lactose, and dipalmitoyl phosphatidylcholine in the ratio of 1:0.5-1.5:1-5 by weight.

* * * * *